United States Patent

Goldenberg

[11] Patent Number: 6,033,369
[45] Date of Patent: Mar. 7, 2000

[54] DISPOSABLE HANDLE AND NEEDLE ASSEMBLY

[76] Inventor: Alec Goldenberg, 4 Washington Sq. Village, #8P, New York, N.Y. 10012

[21] Appl. No.: 09/159,088

[22] Filed: Sep. 23, 1998

[51] Int. Cl.[7] .................................................... A61B 10/00
[52] U.S. Cl. .......................... 600/567; 604/167; 604/170
[58] Field of Search ..................................... 600/562, 566, 600/567; 604/164, 165, 166, 170

[56] References Cited

U.S. PATENT DOCUMENTS

| | | | |
|---|---|---|---|
| 4,596,559 | 6/1986 | Fleischhacker | 604/170 |
| 5,117,838 | 6/1992 | Palmer et al. | 128/772 |
| 5,257,632 | 11/1993 | Turkel et al. | 128/754 |
| 5,331,972 | 7/1994 | Wadhwani et al. | 128/754 |
| 5,423,848 | 6/1995 | Washizuka et al. | 604/167 |
| 5,807,275 | 9/1998 | Jamshidi | 600/567 |

*Primary Examiner*—Cary O'Connor
*Assistant Examiner*—Pamela L. Wingood
*Attorney, Agent, or Firm*—Darby & Darby

[57] ABSTRACT

A disposable biopsy needle of simple construction is disclosed. The biopsy needle includes inner and outer tubes which are affixed, respectively, to a knob and handle assembly. A resiliently flexible lip is positioned within the handle to overlie and constrict the aperture through which the knob is received during assembly of the inner needle and the outer needle. During assembly, the lip deflects as the knob passes into the handle and then returns to an undeflected state once the knob is fully seated within the handle. The lip restrains axial movement of the knob and the inner tube in the fully assembled biopsy needle. The knob may be provided with a knurled surface which engages the free end of a resiliently flexible tab disposed within the handle when the knob is rotated. The interaction of ridges and valleys on the knurled surface with the free end of the flexible tab provides a positive tactile and audible indication of the relative rotation of the inner tube relative to the outer tube. The disposable biopsy needle may be subjected to a sterilization process to provide a sterile biopsy needle. A method for assembling a disposable biopsy needle is also disclosed.

16 Claims, 2 Drawing Sheets

DISPOSABLE HANDLE AND NEEDLE ASSEMBLY

FIELD OF THE INVENTION

The present invention relates to a disposable handle and needle assembly.

BACKGROUND OF THE INVENTION

Disposable needles have been proposed in the art, such as disclosed in allowed U.S. application Ser. No. 08/932,109, filed Sep. 17, 1997, entitled "CONNECTOR FOR REPLACEABLE BIOPSY NEEDLE." That patent application discloses a snap-lock connection for selectively connecting the needle and handle together. The snap-lock connection of the aforementioned patent application better ensures that the needle remains sterile when assembled onto the handle.

Other two-piece needle constructions for retrieving biopsy samples are known from U.S. Pat. Nos. 5,522,398 and 5,634,473 of Goldenberg et al., both of which are assigned to Medsol, Inc., and U.S. Pat. No. 5,429,138 of Jamshidi.

In all of these designs, a complex handle mechanism has been proposed whereas there remains a need in the art to have a unitary, disposable handle and needle assembly which provides a control for the operator to retrieve a biopsy specimen. What is further needed and has not heretofore been available is a disposable handle and needle assembly which is suited for collecting bone marrow biopsy specimens.

SUMMARY OF THE INVENTION

In accordance with one aspect of the present invention, a disposable biopsy needle is disclosed. The biopsy needle includes an outer tube and an inner tube, each having a proximal end and a lumen therein. The inner tube is disposed within the outer tube for rotatable movement therein. The proximal end of the inner tube projects from the proximal end of the outer tube. A knob is affixed to the proximal end of the inner tube and a handle is affixed to the proximal end of the outer tube. The handle has a bore extending therethrough, wherein a distal bore portion is sized to receive the outer tube and a proximal bore portion is sized to receive and seat the knob. The handle further includes a resiliently flexible lip which is positioned to overlie and constrict access to the proximal bore portion. During assembly of the biopsy needle, the lip deflects as the knob passes into the handle and returns to an undeflected state once the knob is fully seated within the proximal bore portion. The lip restrains axial movement of the knob and the inner tube in the fully assembled biopsy needle.

In accordance with yet another aspect of the invention, the knob is provided with a knurled surface which engages the free end of a resiliently flexible tab when rotated relative to the handle. The interaction of the ridges and valleys of the knurled surface of the knob and the free end of the flexible tab provides a positive tactile and audible indication of the relative rotation of the inner tube relative to the outer tube. The tab is deflected by the ridges of the knob upon rotation of the knob and returns to an undeflected state whenever the valleys of the knob are aligned with the tab.

In accordance with another aspect of the invention, the disposable biopsy needle as described above is subjected to a sterilization process to result in a sterile biopsy needle. The sterile biopsy needle is suitable for use in a patient (human or other mammal), or reuse if a previously used biopsy needle has been again subjected to a sterilization process.

In a preferred embodiment, the biopsy needle further includes a stylet which projects from the distal tip of the biopsy needle and is housed within the lumen of the inner tube. The knob affixed to the proximal end of the inner tube preferably has a central throughhole through which the stylet is received. The stylet preferably has a threaded cap affixed to a proximal end thereof which is selectively threadedly engaged to the handle. Also, the cap preferably has a diameter no less than that of the knob, and more preferably has a diameter which is greater than the diameter of the knob.

Yet another aspect of the present invention is a method for assembling a disposable biopsy needle. The method includes the steps of providing outer and inner tubes, each having a respective lumen; affixing a knob to the proximal end of the inner tube; affixing a handle to the proximal end of the outer tube; and seating the knob into the handle. The handle includes a bore therethrough which has a distal bore portion sized to receive the outer tube and a proximal bore portion sized to receive the knob. The step of seating the knob into the handle includes the steps of sliding a distal end of the inner tube into a proximal end of the outer tube; deflecting a resiliently flexible lip positioned to overlie and constrict access to the proximal bore portion as the knob passes over the lip; and permitting the lip to return to an undeflected state once the knob is seated within the proximal bore portion. These assembly steps result in a biopsy needle construction in which axial movement of the knob and the inner tube are restrained, yet the inner tube remains free to rotate relative to the outer tube.

In accordance with a further aspect of the inventive assembly method, the disposable biopsy needle is subjected to sterilization process steps which sterilize the biopsy needle for use or reuse in a patient (human or other mammal).

These and other objects of the present invention will be appreciated from the following detailed description in conjunction with the detailed accompanying drawings.

DISCLOSURE OF THE BEST MODE

By way of overview in introduction, the invention is described in connection with a preferred industrial application of the invention, a biopsy needle and handle assembly 10. The working end of the needle, which severs and retrieves a specimen from a patient, is preferably a snare as described in the aforementioned U.S. Pat. Nos. 5,522,398 and 5,634,473, both of which are incorporated herein as if set forth in their entirety herein.

Figure 1:
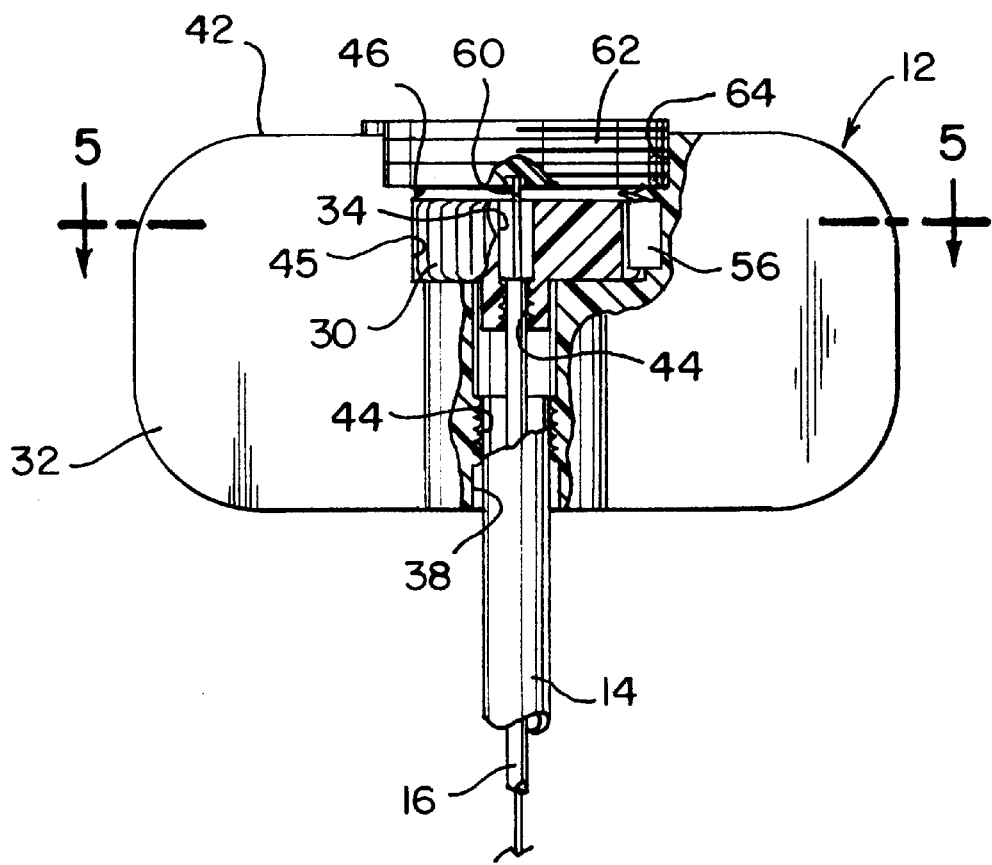
FIG. 1 is a front elevational view, partially broken away, of a needle and handle assembly.
Figure 2:
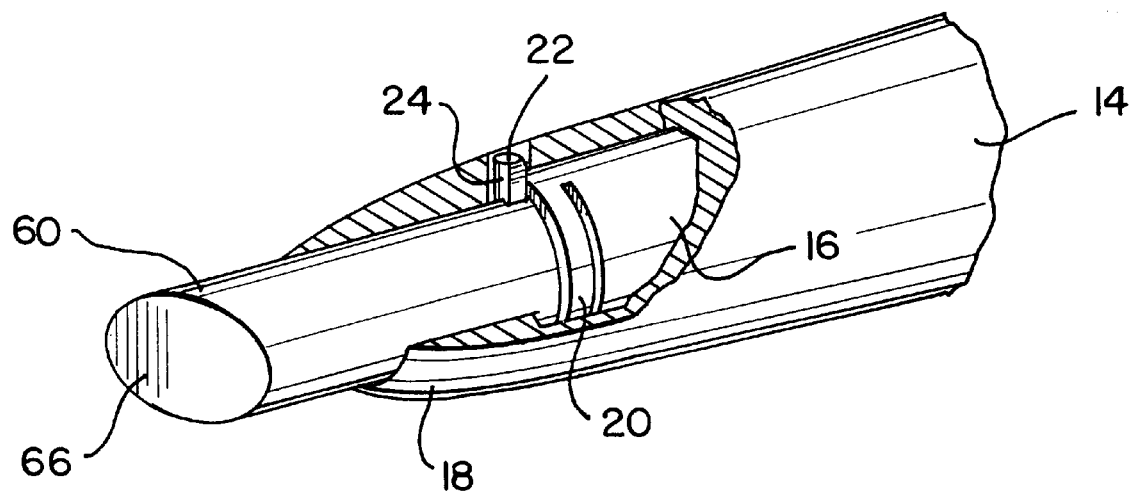
FIG. 2 is a detail perspective view, partially in section, of a distal or working end of the biopsy needle.

FIGS. 1 and 2 show the assembly 10 having a needle 12 comprising outer and inner coaxial tubes 14, 16 which are generally rigid (e.g., are made of hypodermic tubing). Preferably, the inner and outer tubes each define a lumen of a generally constant size. The outer tube 14 terminates in a distally tapering tip 18. The inner tube 16 terminates in a coil or snare 20. The snare 20 may be integral with the inner tube 16, but preferably is injection-molded and affixed at its proximal end to the inner tube 16. A tab or projection 22 extends from the snare 20 to engage the outer tube 14, for example, in a slot 24 within a side wall of the outer tube 14. In a preferred mode, however, the projection(s) 22 extend distally in an axial direction from the snare 20 to engage a proximally facing slot in a cylinder or ring which is affixed to and disposed within the lumen of the outer tube 14, adjacent the distal tip 18. (A cylinder at the distal end of a snare which has a radial projection is shown in the aforementioned U.S. Pat No. 5,634,473 patent.) In operation, relative rotation of the inner tube 16 with respect to the outer tube 14 causes the snare 20 to wind down and grab a biopsy specimen with a force which is sufficient to sever the specimen upon withdrawing the needle 12 from the patient. The snare 20 can be provided with a sharpened or pointed inner surface/edge to better ensure that a sample is removed intact.

The inner tube 16 is rotated relative to the outer tube 14 using a knob 30 and a handle 32, respectively. The handle 32 is affixed to the outer tube 14. The handle has a bore 38 which extends between a distal (bottom) face 40 and a proximal (top) face 42. The proximal end of the outer tube 14 is received within a distal portion of the bore 38. The distal portion of the bore 38 may be sized to be slightly larger than the outside diameter of the outer tube 14, and optionally includes a series of the protuberances 44 which frictionally engage the proximal end of the outer tube to prevent relative movement therebetween. An epoxy or a heat welding step may be used instead of or in addition to the aforementioned protuberances 44 to affix the outer tube 14 to the handle 32. Preferably, the handle 32 is insertion molded directly onto the outer tube 14 in a conventional manner.

A proximal portion of the bore 38 is enlarged relative to the distal portion of the bore 38 for receiving the knob 30. The knob 30 is affixed to the proximal end of the inner tube 16, for example, in the same manner that the handle 32 is affixed to the outer tube 14. Preferably, the inner tube 16 is slightly longer than the outer tube 14 so that the proximal end of the inner tube projects proximal of the outer tube for attachment to the knob 30.

Figure 3:
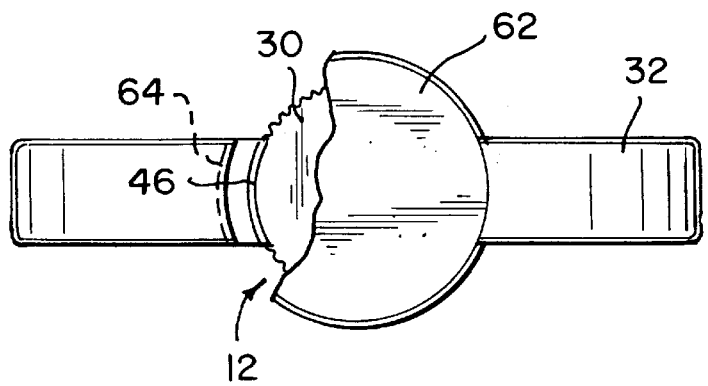
FIG. 3 is a top view, partially broken away, of the assembly of FIG. 1.

As perhaps best seen in FIG. 3, the handle 32 further includes a resiliently flexible lip 46 which overlies the proximal bore portion, and, more particularly, constricts access to the cavity 45 in which the knob is seated. Preferably, the lip 46 is formed of a moderately flexible piece of the same material that is used to form the handle 32 (for example, the lip 46 may be a living hinge or weakened piece of material formed integral with the rest of the handle 32). The knob 30 has a size (that is, diameter, if the knob is round) which is selected to fit within the cavity 45, but which is larger than the aperture 48 to the cavity, delimited by the space between the lips 46. Accordingly, upon insertion of the knob into the cavity 45, the lips 46 are forcibly deflected by the knob 30 as the knob 30 is advanced into the cavity 45. However, once the knob 30 is fully seated within the cavity, the lips 46 return to their undeflected state and restrict withdrawal of the inner tube and knob from the handle 32. In other words, once the lip 46 returns to its undeflected state, the knob 30 is permanently seated within the handle 32-at least within the range of forces that would be applied when the needle is put to use; the knob can be removed by application of suitable force to sterilize the inner tube separate from the outer tube, if desired.

When the biopsy needle assembly 10 is used in accordance with a preferred mode of the invention, then the projection(s) 22 at the distal end of the snare 20 will engage one or more slot(s) 24 in a cylinder affixed to and disposed within the lumen of the outer tube 14 at generally the same moment that the lip 46 is permitted to return to its undeflected state and that the knob is seated, provided, of course, that the projection(s) 22 are rotationally aligned with the slot(s) 24.

The knob and inner tube assembly 30, 16 is inserted into the bore 38 from the proximal face 42 of the handle 32. The distal end of the inner tube 16 is advanced into the handle 32 and advanced into the lumen of the outer tube 14. The inner tube is continually advanced until a distal face of the knob 30 engages the lips 46 at the entrance to the cavity 45. Further advancement of the knob 30 causes the lips 46 to deflect for so long as the knob 30 abuts the lips. Once the knob 30 has been sufficiently advanced toward the distal face 40 of the handle, the knob 30 will clear the lips 46 and the lips will resiliently return to their undeflected state.

Figure 4:
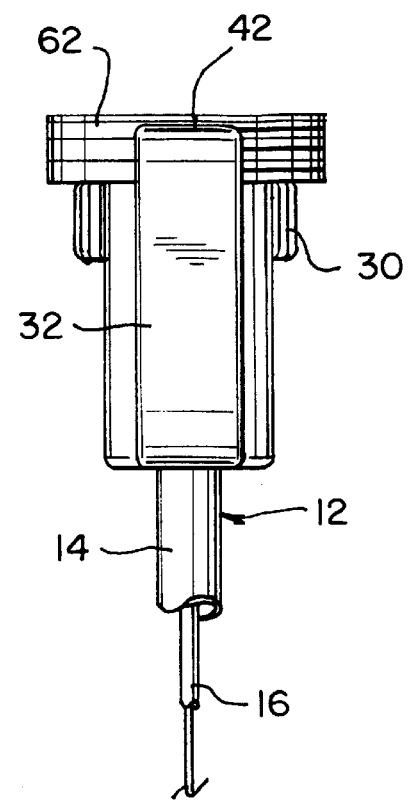
FIG. 4 is a side view of the assembly of FIG. 1.

With reference to FIG. 4, a side view of the assembly 10 illustrates the knob 30 protruding from the handle 32 for ease of rotation by the operator; however, the particular shape of the handle 32 forms no part of the instant invention.

Figure 5:
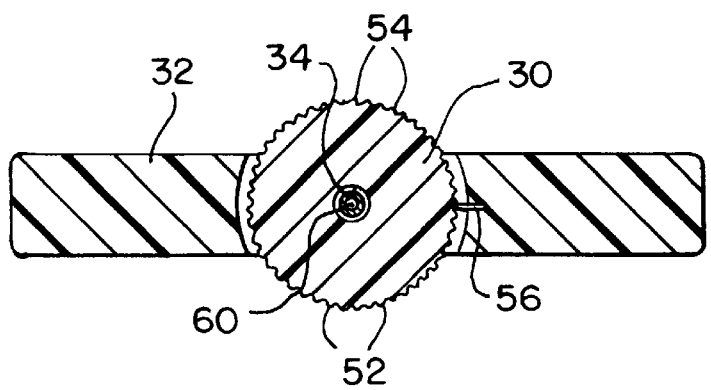
FIG. 5 is a sectional view taken along line 3—3 of FIG. 1.

Turning now to FIG. 5, a sectional view of the handle is illustrated showing the knob 30, fully seated within the cavity 45. Preferably, the knob 30 has knurled outer surface including a plurality of ridges 52 separated by valleys 54. The knurled surface of the knob 30 provides a good friction surface which is engaged by the operator to affect rotation of the inner tube relative tube 14.

In accordance with a further aspect of the present invention, a pawl or tab 56 is provided within the cavity 45 and positioned to engage the ridges 52 of the knob and to restrain rotatable movement of the knob. Preferably, the tab is affixed at one margin to the handle 32 and has an opposite margin which engages ridges 54. The tab is resiliently flexible and is deflected by the ridges upon rotation of the knob 30 in response to a manual force applied by the operator. As the knob 30 rotates, the ridges 52 deflect the free end 58 of the tab 56 until a next valley 54 is aligned with the tab 56 (as shown in FIG. 5). Due to the natural resiliency of the tab 56, the tab returns to an undeflected state whenever it is aligned with one of the valleys. As a result, both a tactile and audible click are provided by the interaction of the tab 56 with the knurled surfaced of the knob. Thus, the operator has a positive indication of the rotation of the inner tube relative to the outer tube, which in the context of a biopsy needle, indicates that the biopsy-grabbing element (e.g., the snare 20) is being actuated to grab a sample. In addition, the tab 56 ensures that the inner tube 16 moves relative to the outer tube 14 only when a force is applied to the knob 30, and not thereafter. In other words, once rotated in a first direction, the knob will not tend to rotate back to its initial position due to the frictional coupling between the tab 56 and the ridges 52.

Referring again to FIGS. 1 and 2, the biopsy needle and handle assembly 10 may further include a stylet 60 which is received within the lumen of the inner tube 16 and which projects from the needle 12. As understood by those of skill in the art, the stylet 60 assists in penetrating the patient's skin and accessing the site from the which the sample is to be extracted. At the proximal end of the stylet 60 is a cap 62 which is threadedly engaged at the proximal face 42 of the handle. As shown in FIGS. 1 and 3, a proximal portion of the bore 38 includes threadings 64 which mates with the threads on the cap 62. The stylet is inserted into the throughhole of the knob 30 and advanced through the inner tube 16 until it projects from the distal end of the needle 12. Preferably, the cap 62 is affixed to the stylet 60 in the same manner that the knob 30 is attached to the inner tube 16, and in the same manner that the handle 32 is attached to the outer tube 14. To complete the insertion of the stylet into the needle and handle assembly 10, the cap 62 is threadedly engaged to the handle 32 using mating threads 64 of the handle.

The stylet 16 may include an angled face 66 which can be oriented (by manipulating the cap 62) to match any angle that may be imparted to the distal tip of the needle 12.

Preferably, the cap 62 has a diameter which is no less than that of the knob 30 and, more preferably, has a diameter which is greater than that of the knob. As can be appreciated from FIG. 4, by providing a cap 62 which is greater in diameter than that of the knob 30, the stylet 60 can be separated from the handle 32 without the operator inadvertently manipulating the knurled knob 30. In other words, the larger diameter cap 62 can be unthreaded from the handle 32 with minimal risk of inadvertently actuating the element which grabs the biopsy sample. Once the needle and handle assembly 10 have penetrated the patient's skin to a predetermined and desired distance, the cap is unthreaded from the mating threads 64 of the handle, and the stylet 60 is removed from the needle and handle assembly 10. At that point, the needle and handle assembly 10 are advanced together into the patient with a core sample being simultaneously received within the lumen of the inner tube 16. The biopsy specimen can then be grabbed and removed from the patient by any one of the number of elements or means, including the above-mentioned snare 20.

The disposable biopsy needle of the present invention is particularly well suited for single-use applications because the assembled biopsy needle can be sterilized and packaged in a sterile condition. Preferably, each assembly 10 is sterilized and packaged in an individual pouch, for example, a hermetically sealed plastic bag. The needle 12 is intended for one use only and is non-sterile after it is inserted into a patient. Likewise, if the needle contacts a nonsterile surface, or if the package remains open and the needle is not put into service, the sterility of the needle is compromised. However, the needle may be sterilized again and reused. The process of sterilizing the needle can take place in accordance with any number of conventional ways including heat treatment and an autoclave or a chemical or vapor cleansing process, as understood by those of skill in the art.

Preferably, sterilization is accomplished on the needle and handle assembly 10 using an ethylene oxide processing cycle which includes preconditioning, exposure to ethylene oxide (EtO), and aeration. Preconditioning preferably includes exposure to a 60%±20% humidity at 37.80° C.±5.6° C. for eight hours or more.

The EtO exposure preferably includes 100% EtO (ethylene oxide) as the sterilant within a vessel which, after loading the assembly 10, is heated to about 48.9° C. and then evacuated to 0.5 psia or less. Then, steam is injected into the vessel to achieve a relative humidity of about 60%±20%. Once this level of humidity is achieved the vessel is maintained for a dwell time of about 60 to about 80 minutes. The EtO gas is injected into the vessel which is also provided with nitrogen gas. The nitrogen gas provides a gas blanket which minimizes certain risks attendant with handling EtO (EtO is explosive). In particular, 7.5 psia ±0.5 psia nitrogen gas is injected into the vessel, and then, after a short dwell time to ensure nitrogen gas dissipation within the vessel, EtO is injected to a pressure of about 5.6 psia ±0.3 psia into the vessel. During sterilization, some EtO may be absorbed by assembly 10, and so extra EtO may be added as necessary throughout a six to seven hour dwell period to maintain the EtO concentration at an average of 635 mg/l±45 mg/l. Then, the EtO and nitrogen gases are evacuated, and the vessel is flushed repeatedly (for example, four times) with nitrogen gas at elevated pressure (for example, 14.1±0.5 psi). Finally, the vessel is purged with air, and the assembly is ready for aeration.

Aeration preferably occurs in two stages. First, the assembly 10 is placed in a negative pressure environment and heated to about 32.2° C.±8.3° C. for sixteen or more hours. Then, the assembly is heated to 48.9° C.±8.3° C. and held at that temperature for sixteen or more hours.

Of course, sterilization can occur in other ways, the foregoing being fully descriptive of one mode of sterilizing the assembly 10, and not necessarily the best mode.

Although the biopsy needle is intended to be disposed after single use, depending on the design of the element which grabs and severs a sample (e.g., the snare 20), the needle can be reused. Other designs, such as disclosed by Hallac in U.S. Pat. No. 3,605,721, undergo plastic deformation when a sample is grabbed and are not suitable for reuse. However, other designs such as in the aforementioned Goldenberg et al. patents, include an elastically resilient snare element which can be reused under certain circumstances. In particular, provided the biopsy needle has undergone an appropriate sterilization process to free the needle of any bacteria, the needle can be reused. The process of sterilizing the biopsy needle, therefore, results in a distinct product, namely one which is suitable for use in a mammal (a human or other animal) as opposed to one which is not.

The aforementioned Jamshidi is hereby incorporated by reference as if set forth in their entireties herein.

From the foregoing description, it will be clear that the present invention may be embodied in other specific forms without departing from the spirit or essential characteristics thereof. The presently disclosed embodiment is therefore to be considered in all respects as illustrative and not restrictive, the scope of the invention being indicated by the appended claims, and not limited to the foregoing description.

I claim:

1. A disposable biopsy needle, comprising:
    an outer tube defining a first lumen, the outer tube having a proximal end and a tapering distal tip;
    an inner tube defining a second lumen, the inner tube being disposed within the outer tube for rotatable movement therein and having a proximal end which extends proximal to the proximal end of the outer tube;
    a knob affixed to the proximal end of the inner tube; and
    a handle affixed to the proximal end of the outer tube, the handle having a bore therethrough, the bore including a distal bore portion which is sized to receive the outer tube and a proximal bore portion which is sized to receive the knob,
    wherein the knob is seated within the proximal bore portion,
    wherein the handle further includes a resiliently flexible lip positioned to overlie and constrict access to the proximal bore portion, the lip being deflected during insertion of the knob into the handle and returning to an undeflected state once the knob is seated within the proximal bore portion, whereby axial movement of the knob and the inner tube are restrained.

2. The disposable biopsy needle as in claim 1, wherein the disposable biopsy needle is sterile.

3. The disposable biopsy needle as in claim 1, wherein the knob has a throughhole, the biopsy needle further comprising:

a stylet having a proximal end, the stylet being received in the throughhole and in the second lumen of the inner tube, a threaded cap affixed to the proximal end of the stylet, the cap having a diameter no less than that of the knob, the cap being threadedly engaged to the handle.

4. The disposable biopsy needle as in claim 3, wherein stylet cap is greater diameter than the knob.

5. The disposable biopsy needle as in claim 3, wherein the disposable biopsy needle is sterile.

6. The disposable biopsy needle as in claim 1, wherein the proximal bore portion is larger than the distal bore portion.

7. The disposable biopsy needle as in claim 1, wherein the knob has a knurled surface which includes alternating ridges and valleys, and wherein the handle includes a resiliently flexible tab having one margin affixed within the proximal bore portion of the handle and an opposing margin positioned to engage the ridges of the knob and restrain rotatable movement thereof, the tab being deflected by the ridges upon rotation of the knob and returning to an undeflected state when aligned with the valleys.

8. The disposable biopsy needle as in claim 3, wherein the disposable biopsy needle is sterile.

9. A method for assembling a disposable biopsy needle, comprising the steps of:

providing an outer tube defining a first lumen, the outer tube having a proximal end and a tapering distal tip;

providing an inner tube defining a second lumen, the inner tube being disposed within the outer tube for rotatable movement therein and having a proximal end which extends proximal to the proximal end of the outer tube;

affixing a knob to the proximal end of the inner tube; and affixing a handle to the proximal end of the outer tube, the handle having a bore therethrough, the bore including a distal bore portion which is sized to receive the outer tube and a proximal bore portion which is sized to receive the knob, seating the knob into the handle by:

sliding the distal end of the inner tube into the proximal end of the outer tube;

deflecting a resiliently flexible lip positioned to overlie and constrict access to the proximal bore portion as the knob passes over the lip; and permitting the lip to return to an undeflected state once the knob is seated within the proximal bore portion, whereby axial movement of the knob and the inner tube are restrained.

10. The method as in claim 9, including the additional step of sterilizing the disposable biopsy needle.

11. The method as in claim 9, wherein the knob has a throughhole, including the additional steps of:

providing a stylet in the throughhole and in the second lumen of the inner tube; and threadedly engaging a proximal end of the stylet to the handle.

12. The method as in claim 11, including the additional step of sterilizing the disposable biopsy needle.

13. The method as in claim 9, wherein the knob has a knurled surface which includes alternating ridges and valleys, including the additional step of:

positioning one margin of a resiliently flexible tab to engage the ridges of the knob and restrain rotatable movement thereof, another margin of the tab being affixed within the proximal bore portion of the handle.

14. The method as in claim 13, including the additional step of sterilizing the disposable biopsy needle.

15. The method as in claim 9, wherein at least one of the affixing steps includes injection molding at least one of the knob and the handle onto the inner tube and outer tube, respectively.

16. The method as in claim 9, wherein the step of sliding the distal end of the inner tube includes the step of aligning a distally extending projection at the distal end of the inner tube with a proximally extending slot at the distal end of the outer tube.

* * * * *